US00PP27713P3

(12) United States Plant Patent
Suzuki

(10) Patent No.: US PP27,713 P3
(45) Date of Patent: Feb. 28, 2017

(54) ***LOROPETALUM* PLANT NAMED 'IRODORI'**

(50) Latin Name: *Loropetalum chinense*
Varietal Denomination: IRODORI

(71) Applicant: Yuji Suzuki, Kawaguchi (JP)

(72) Inventor: Yuji Suzuki, Kawaguchi (JP)

(73) Assignee: Spring Meadow Nursery, Inc, Grand Haven, MI (US)

( * ) Notice: Subject to any disclaimer, the term of this patent is extended or adjusted under 35 U.S.C. 154(b) by 83 days.

(21) Appl. No.: 14/544,872

(22) Filed: Feb. 26, 2015

(65) Prior Publication Data

US 2016/0262296 P1 Sep. 8, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Loropetalum* cultivar named 'IRODORI' is disclosed, characterized by bright pink, white, green and maroon variegated foliage, tall upright and spread habit and bright pink flowers with some flower re-bloom after the initial heavy Spring bloom. The new variety is a *Loropetalum*, normally produced as an outdoor garden or container plant.

2 Drawing Sheets

Figure 1:
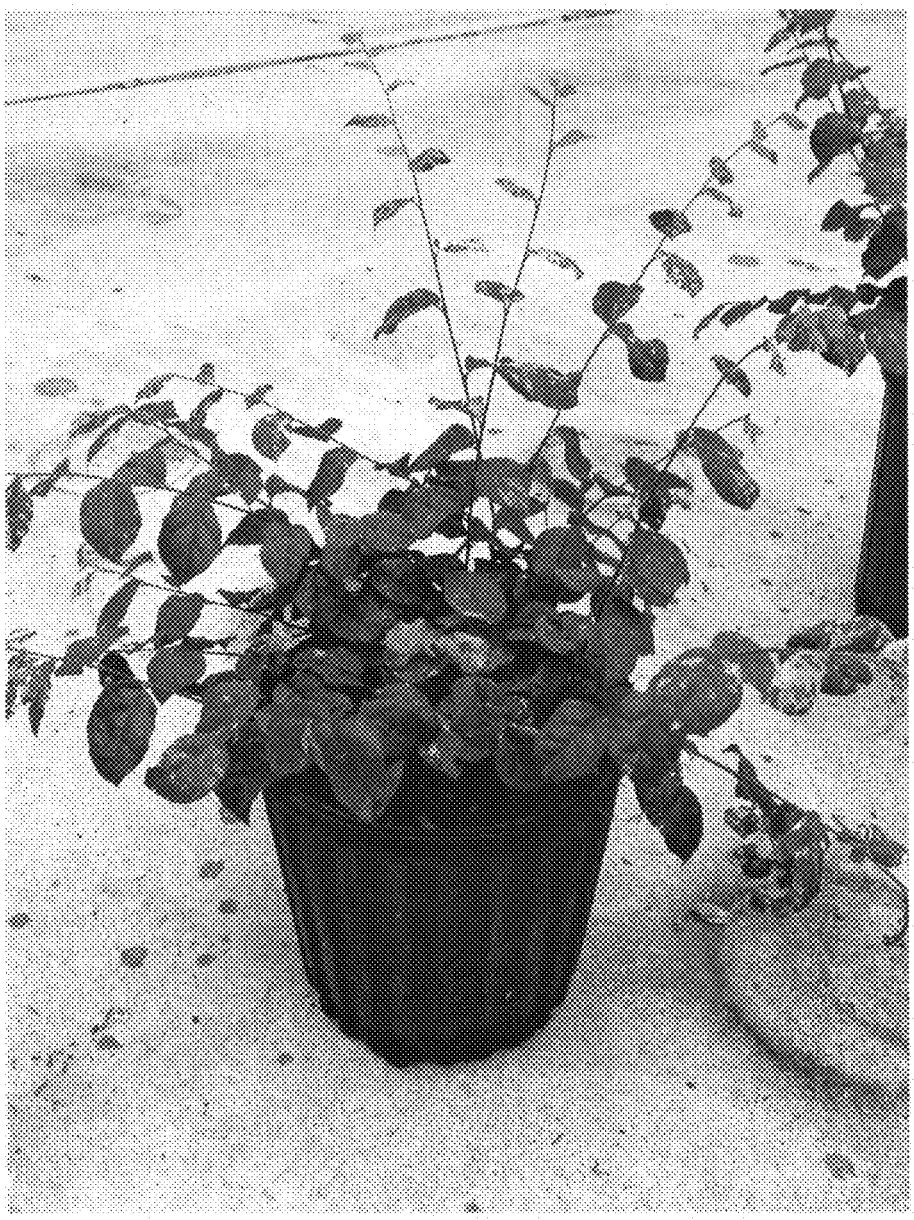

Latin name of the genus and species: *Loropetalum chinense*.

Variety denomination: 'IRODORI'.

BACKGROUND OF THE INVENTION

The new *Loropetalum* cultivar is a product of a planned breeding program conducted by the inventor, Yuji Suzuki, in Kawaguchi City, Saitama, Japan. The objective of the breeding program was to produce new *Loropetalum* varieties with better foliage color and improved flowering for ornamental commercial applications. The cross resulting in this new variety was made during Apr. 24, 2004.

The seed parent is the, unpatented, commercial variety referred to as *Loropetalum* 'Kinsai'. The pollen parent is the unpatented, propriety variety referred to as *Loropetalum* '3-28'. The new variety was discovered in a commercial nursery by the inventor in a group of seedlings resulting from the 2004 crossing, in Kawaguchi City, Saitama, Japan.

Asexual reproduction of the new cultivar was performed by softwood cuttings. This was first performed at a commercial nursery in Kawaguchi City, Saitama, Japan, in 2009 and has shown that the unique features of this cultivar are stable and reproduced true to type in 5 successive generations.

SUMMARY OF THE INVENTION

The cultivar 'IRODORI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'IRODORI' These characteristics in combination distinguish 'IRODORI' as a new and distinct *Loropetalum* cultivar:

1. Bright and well variegated foliage with pink, white, slight undertones of green and maroon colors.
2. Tall, upright and spreading plant, reaching 4 to 6 feet tall.
3. Stunning bright pink flower that complement the variegated foliage.
4. Some re-bloom occurs after the initial heavy Spring flowering.

Plants of the new cultivar 'IRODORI' are similar to plants of the seed parent, *Loropetalum* 'Kinsai' in most horticultural characteristics, however, plants of the new cultivar 'IRODORI' differ in the following;

1. Bright red/pink flowers. The seed parent flower color is red.
2. Upright and outwardly spreading growth habit. The seed parent growth habit is only upright.
3. Foliage shape is broad ovate. The parent foliage shape is ovate.
4. Brighter foliage variegation of pink, white, green and maroon. The seed parent foliage color is more subdued and only white, scarlet and purple.

Plants of the new cultivar 'IRODORI' are similar to plants of the pollen parent, *Loropetalum* '3-28' in most horticultural characteristics, however, plants of the new cultivar 'IRODORI' differ in the following;

1. Bright red/pink flowers; the pollen parent flower color is scarlet.
2. Upright and spreading growth habit; the pollen parent growth habit is only spreading.
3. Back of leaf color is a lighter shade of green.
4. Brighter foliage variegation of pink, white, green and maroon; the parent pollen parent is only variegated with white.

COMMERCIAL COMPARISON

Plants of the new cultivar 'IRODORI' are comparable to the patented, commercial variety *Loropetalum* 'Shang-hi'

U.S. Plant Pat. No. 18,331. The two *Loropetalum* varieties are similar in most horticultural characteristics; however, the new variety 'IRODORI' differs in the following:

1. Upright and somewhat open, free branching growth habit. The comparator growth habit is upright and more densely branched.
2. Bright foliage variegation of pink, white, green and maroon. The comparator foliage is solid dark purple.
3. Degree of variegation changes throughout the season becoming most prominent in late Summer and Fall. The comparator holds same color all season.

BRIEF DESCRIPTION OF THE PHOTOGRAPHS

The accompanying photograph in FIG. 1 illustrates in full color a typical plant of 'IRODORI' grown in a 1 gallon pot. Age of the plant photographed is approximately 1 to 2 years old from a rooted cutting.

Figure 2:
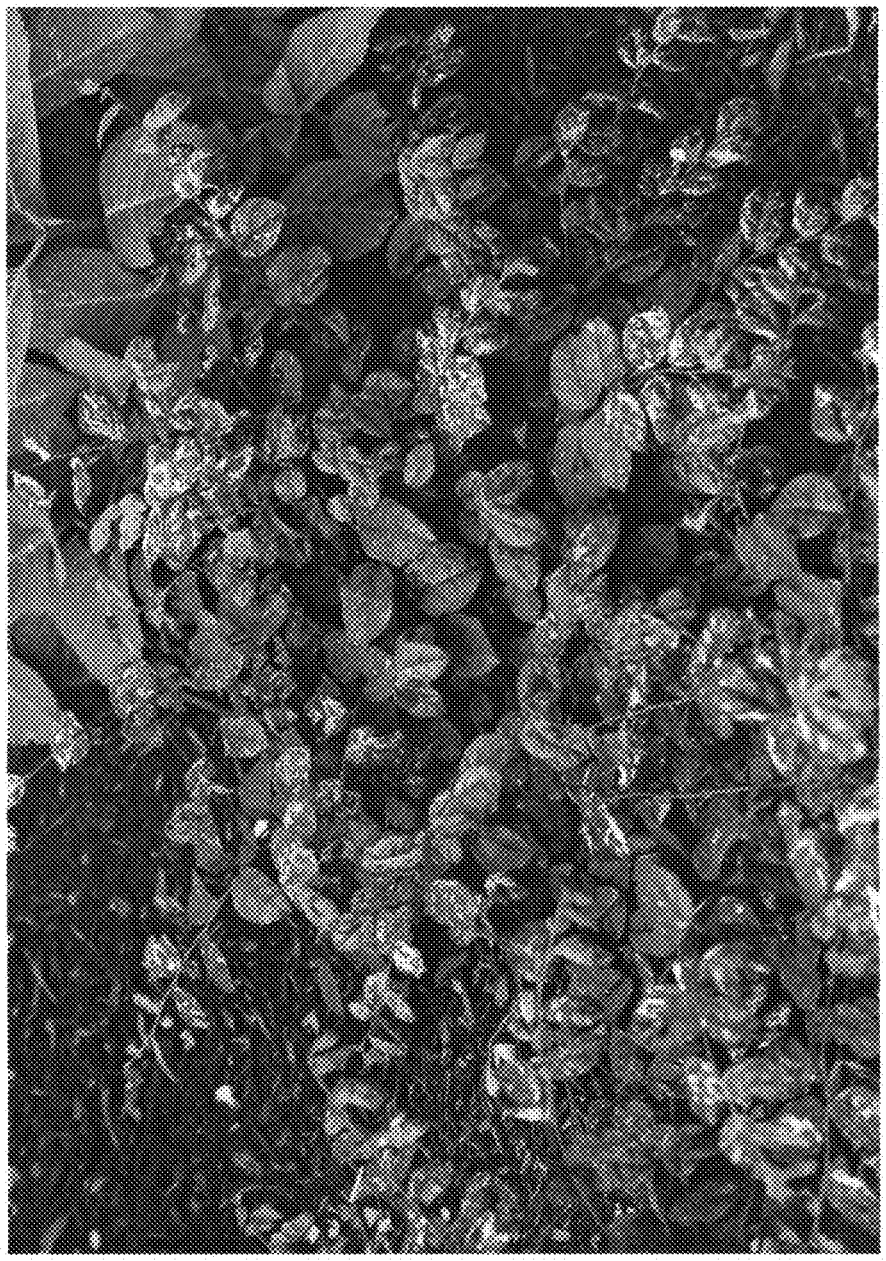

FIG. 2 illustrates the foliage, around July 2014.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'IRODORI' plants grown in a greenhouse, in Grand Haven Mich. The growing temperature averaged from 60° F. to 65° F. during the day and from 40° F. to 50° F. during the night. Growing conditions are double poly from Fall through Winter and shade cloth through the Summer. Measurements and numerical values represent averages of typical plant types.

Botanical classification: *Loropetalum* 'IRODORI'.

PROPAGATION

Type of propagation typically used: Cutting.
Time to initiate roots: 18 days at 27° C.
Number of days to produce a rooted liner in summer: 110 days at 27° C.
Root description: Medium to thick, fibrous, free branching and fleshy. New roots are purple in color, aging to brown.

PLANT

Type of plant: Perennial shrub.
Age of plant described: Approximately 1.5 to 2 years old.
Container size of the plant described: 2 gallon.
Growth habit: Mounded upright.
Height: 4 to 6 feet.
Plant spread: 4 feet.
Growth rate: Good.
Plant vigor: Good.
Branching characteristics: Horizontally emerging branches, originating from base of plant. Angle between 0-45°.
Length of primary lateral branches: 41.6 cm.
Diameter of lateral branches: 3 cm.
Quantity of primary lateral branches: 20.
Characteristics of primary lateral branches:
*Form*.—Round.
*Diameter*.—0.5 cm.
*Color*.—Young stems: Near RHS Greyed-orange 176A. Older stems: Near RHS Greyed-orange 165A.
*Aspect*.—Straight.
*Strength*.—Good.
*Texture*.—Stem pubescence, more prevalent in younger stems.
Internode length: 1.5 cm.

Foliage:

Leaf:
*Arrangement*.—Alternate, Single.
*Quantity*.—Approximately 93 per branch.
*Average length*.—1.5-4.5 cm.
*Average width*.—0.9-3.3 cm.
*Shape of blade*.—Ovate rounded.
*Apex*.—Acute.
*Base*.—Oblique.
*Margin*.—Entire to partially sinuate.
*Texture of top surface*.—Slightly rough due to pubescence.
*Texture of bottom surface*.—Ribbed due to protruding veins and course due to pubescence.
*Color*.—Young foliage represents Spring coloration. Mature foliage Summer coloration. Fall color: Upper side: Near RHS Greyed-Orange 167B with 168A, small amount of 169A and Greyed-Green 197A. Under side: Glaucous, near RHS Greyed-Green 197A, mottled Greyed-Orange 167B with 168A. Young foliage upper side: Near RHS Red-purple 75A and Red-purple 71B in young leaves to Orange-white 159C with mottled overlay of Black 202A. Young foliage under side: Glaucous. Near RHS Red-purple 59A. Mature foliage upper side: Continued mottling of Near RHS Red-purple 75A, Red-purple 71B and Orange-white 159C with larger patches of Black 202A, becoming solid Black 202A with slight undertones of green and red. Mature foliage under side: Glaucous. Near RHS Greyed-green 191A overlaying Greyed-purple 186B.
*Venation*.—Type: Pinnate. Venation color upper side: Midribs and veins are depressed on the upper side. Only distinct color detection on lighter variegated leaves Near RHS Greyed-red 182C. Venation color under side: Midribs and veins are prominent on the underside. Near RHS Greyed-purple 186B.
*Petiole*.—Length: 0.25 to 0.5 cm. Diameter: 1.0 mm. Color: Younger: Near RHS Greyed-purple 183B. Older: Near RHS Greyed-red 182B.

Flower:

Arrangement: At terminal end of branch.
Inflorescence and flower type and habit: Perfect flowers, comprised of strap-shaped petals, occurring in terminal (mainly) and axillary (occasionally) umbels.
Quantity of flowers per inflorescence: 6-7.
Persistent or self-cleaning: Strap-shape, self-cleaning.
Flowering habit: Terminal and axial along stem.
Flower aspect: Upright and outward.
Quantity of flowers per lateral stem: 14-30.
Quantity of flowers per plant: 70-500 depending on size and maturity of the plant.
Natural flowering season: Spring and some Fall re-bloom.
Fragrance: None.

Bud:

*Shape*.—Round.

*Length*.—2 mm.

*Diameter*.—2.5 mm.

*Color*.—Near RHS Red-purple 59B.

Petals:

*Quantity per flower*.—4.

*Shape*.—Linear, not fused.

*Margin*.—Entire.

*Length:* 2.5-3 cm.

*Width:* 3-5 mm.

*Apex*.—Slightly retuse and petals are curled at the tips.

*Color*.—When opening: Upper surface: Near RHS Red-purple 71A. Lower surface: Near RHS Red-purple 71A. Fully opened: Upper surface: Near RHS Red-purple 71A. Lower surface: Near RHS Red-purple 71A.

Sepals:

*Quantity per flower*.—4.

*Appearance*.—Slightly pubescent.

*Arrangement*.—Whorl.

*Shape*.—Ovate and fused, slightly curled outward.

*Length*.—4 mm.

*Width*.—3 mm.

*Apex*.—Acute.

*Base*.—Fused.

*Margin*.—Entire, smooth.

*Color*.—Upper Side: Near RHS Red-purple 71B slightly glaucous. Under side: Near RHS Red-purple 61B.

REPRODUCTIVE ORGANS

Stamens:

*Number*.—4.

Pistil:

*Number*.—2.

OTHER CHARACTERISTICS

Disease/pest resistance: No unusual susceptibility to diseases or pets noted to date.

Drought tolerance: Moderate to good drought tolerance once established.

Temperature tolerance: Typical for *Loropetalum*, with a maximum low temperature tolerance to USDA zone 7.

What is claimed is:

1. A new and distinct cultivar of *Loropetalum* plant named 'IRODORI' as herein illustrated and described.

* * * * *